United States Patent [19]

Harte

[11] 4,144,452
[45] Mar. 13, 1979

[54] FLUOROMETRIC SYSTEM, METHOD AND TEST ARTICLE

[75] Inventor: Richard A. Harte, Redwood City, Calif.

[73] Assignee: International Diagnostic Technology, Inc., Santa Clara, Calif.

[21] Appl. No.: 845,669

[22] Filed: Oct. 26, 1977

Related U.S. Application Data

[63] Continuation of Ser. No. 703,579, Jul. 8, 1976, Pat. No. 4,056,724, which is a continuation-in-part of Ser. No. 447,574, Mar. 4, 1974, Pat. No. 3,913,687, and a continuation-in-part of Ser. No. 553,582, Feb. 27, 1975, Pat. No. 3,992,631.

[51] Int. Cl.² .............................................. G09K 3/00
[52] U.S. Cl. ................................... 250/302; 250/373; 250/461 R
[58] Field of Search ............................... 250/302, 461

[56] References Cited

U.S. PATENT DOCUMENTS 3,992,631  11/1976  Harte .................................... 250/302
4,056,724  11/1977  Harte .................................... 250/302

*Primary Examiner*—Harold A. Dixon
*Attorney, Agent, or Firm*—Limbach, Limbach & Sutton

[57] ABSTRACT

A fluorometric system to determine the kind and amount of substances derived from a biological fluid (e.g., serum or urine) or tissue in which the substances to be detected (e.g., antigen, antibody, hormone or enzyme) are coated onto a substrate surface in fluorescent form. Multiple coating areas of different samples may be employed. The fluorometric system includes a source of filtered light to excite fluorescence, an optical system for conducting the excitation light to such coating, and optical systems for receiving emitted fluorescence and for detecting the same. The system efficiency and optical characteristics disclosed avoid photobleaching; limit fading; and are especially adapted to provide accurate surface reading fluorometry.

1 Claim, 18 Drawing Figures

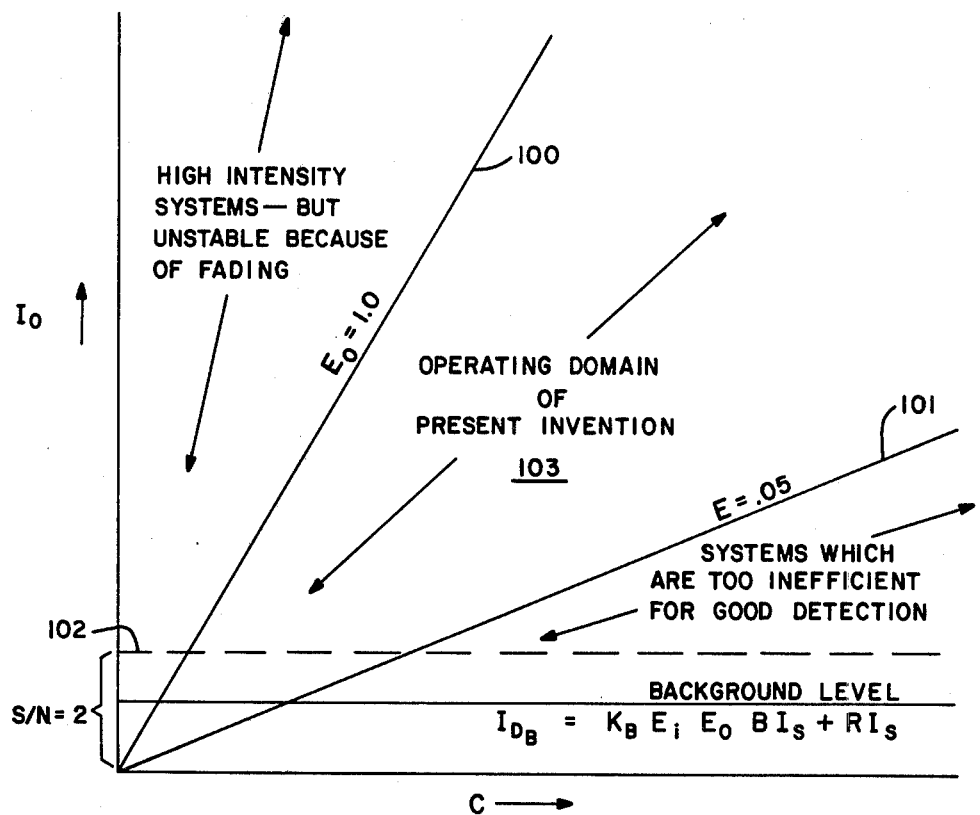
FIG.—7
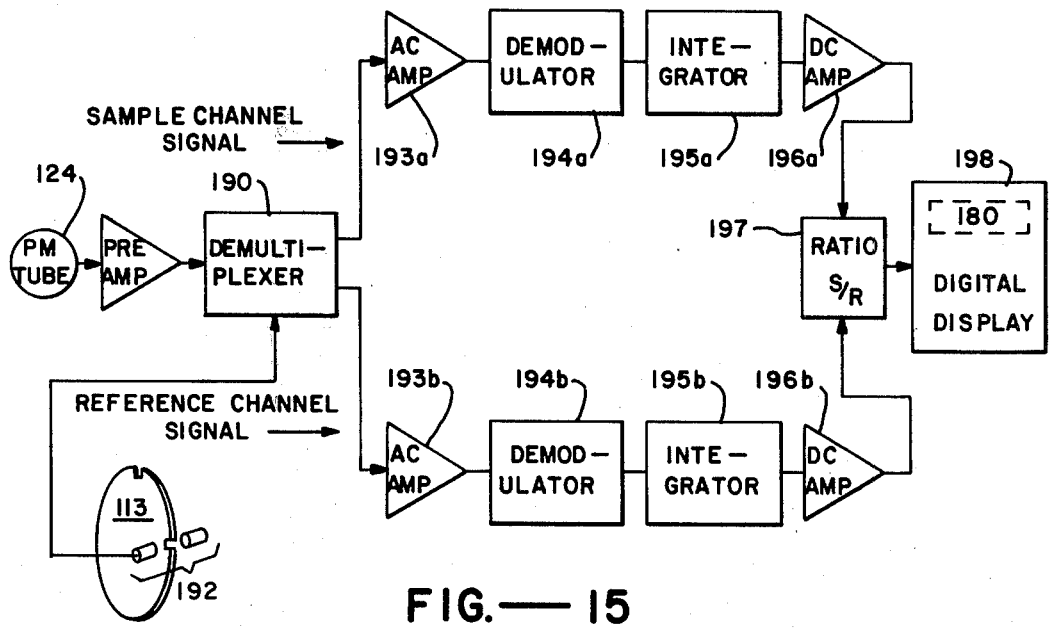
FIG.—15

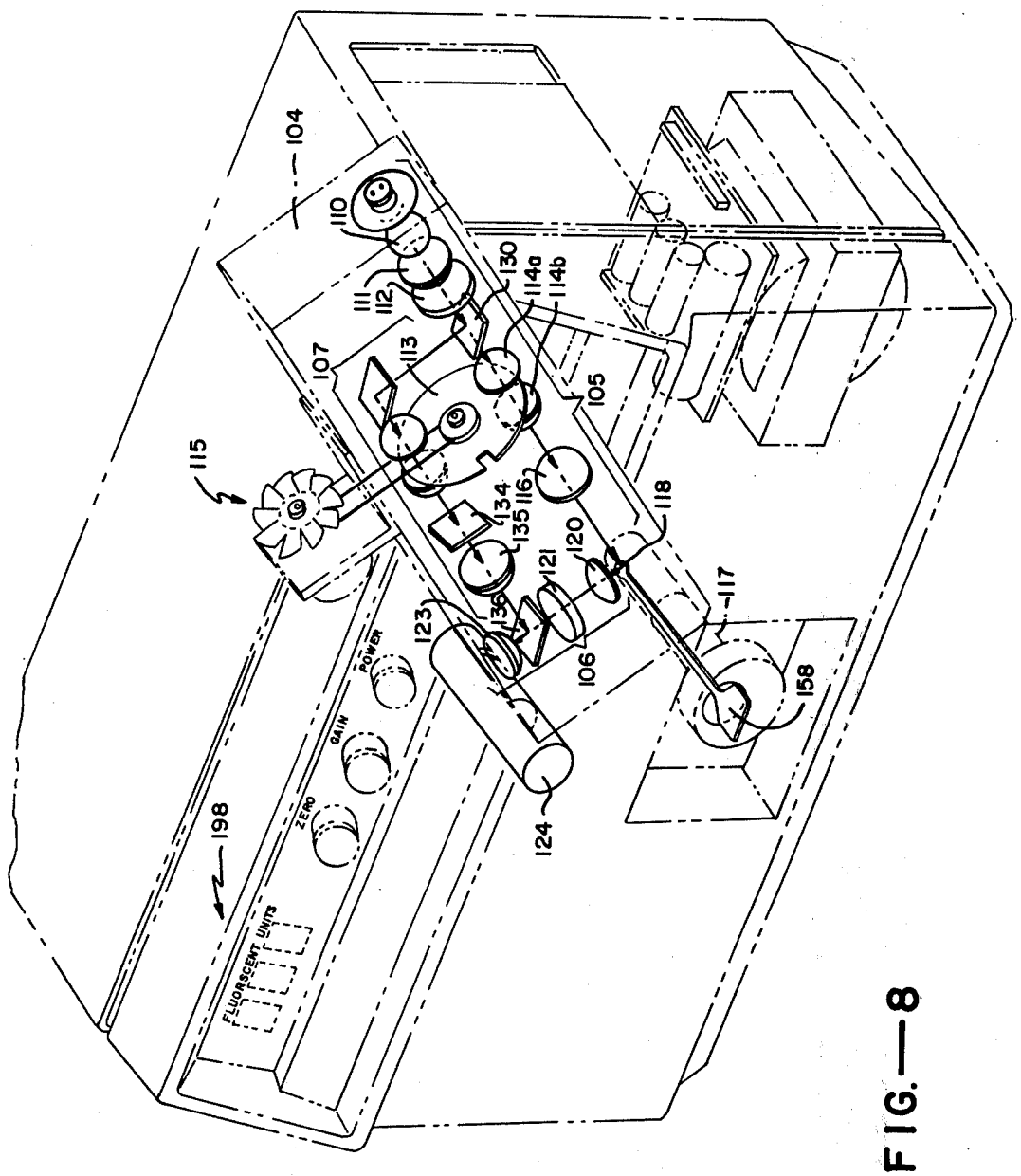
FIG.—8

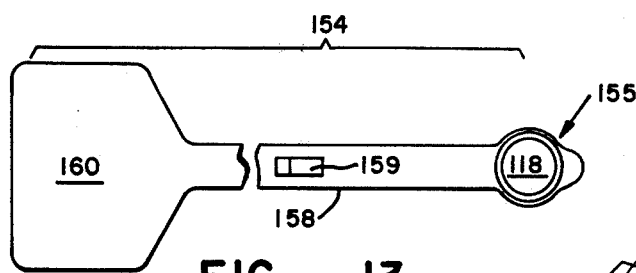
FIG.—13
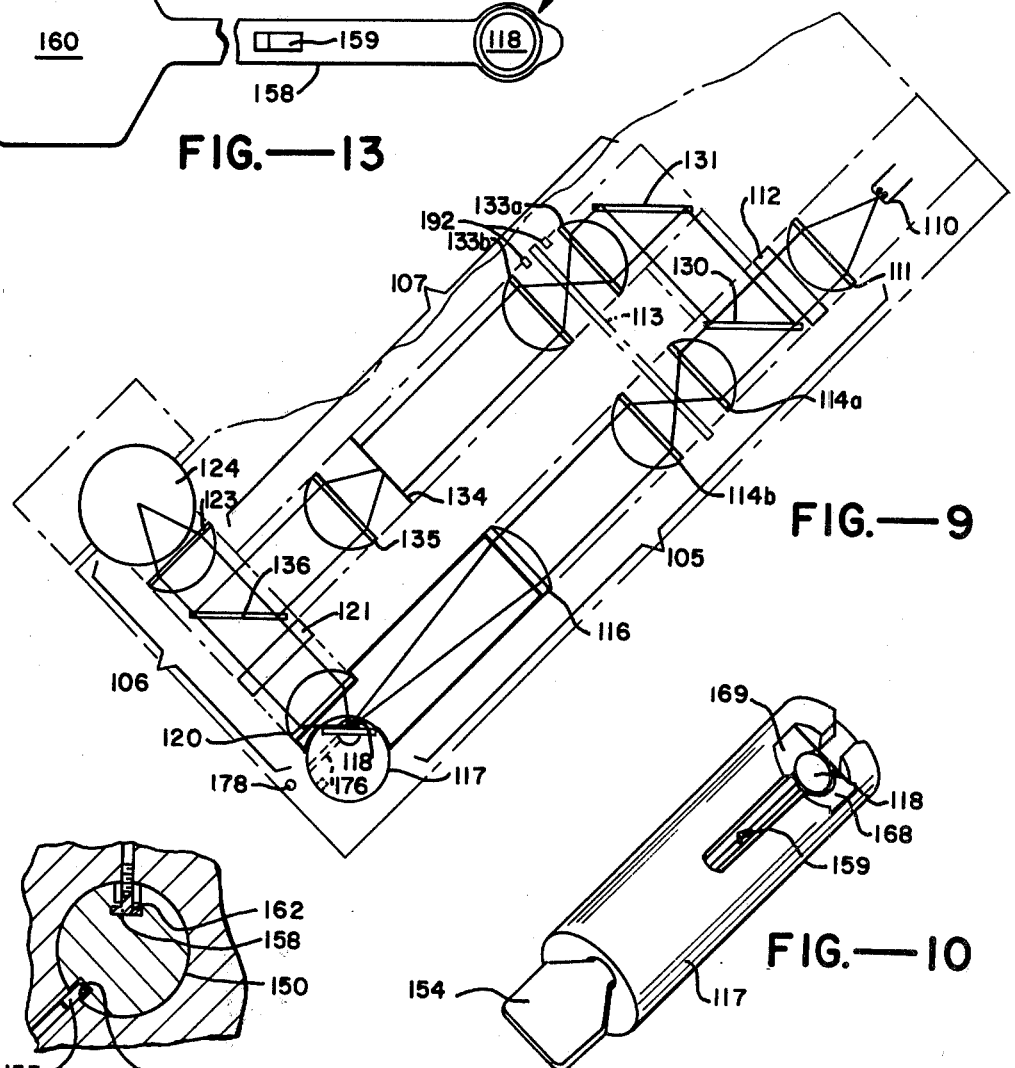
FIG.—9
FIG.—10
FIG.—12
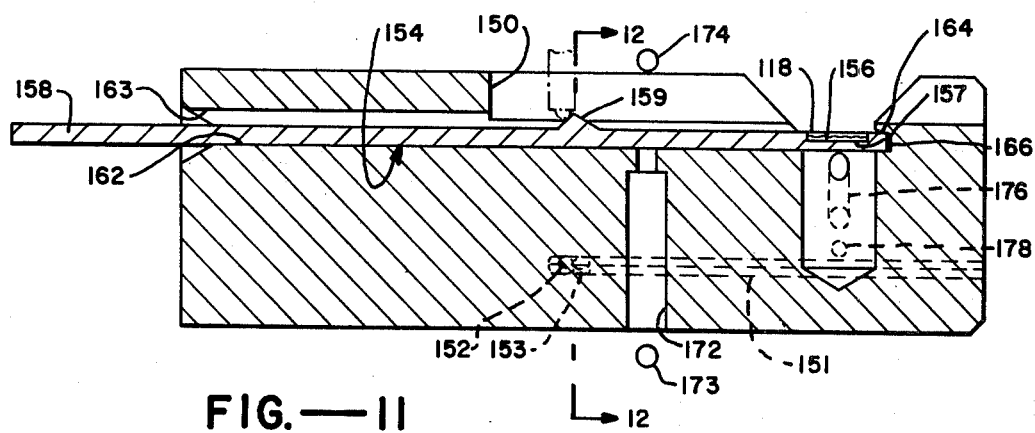
FIG.—11

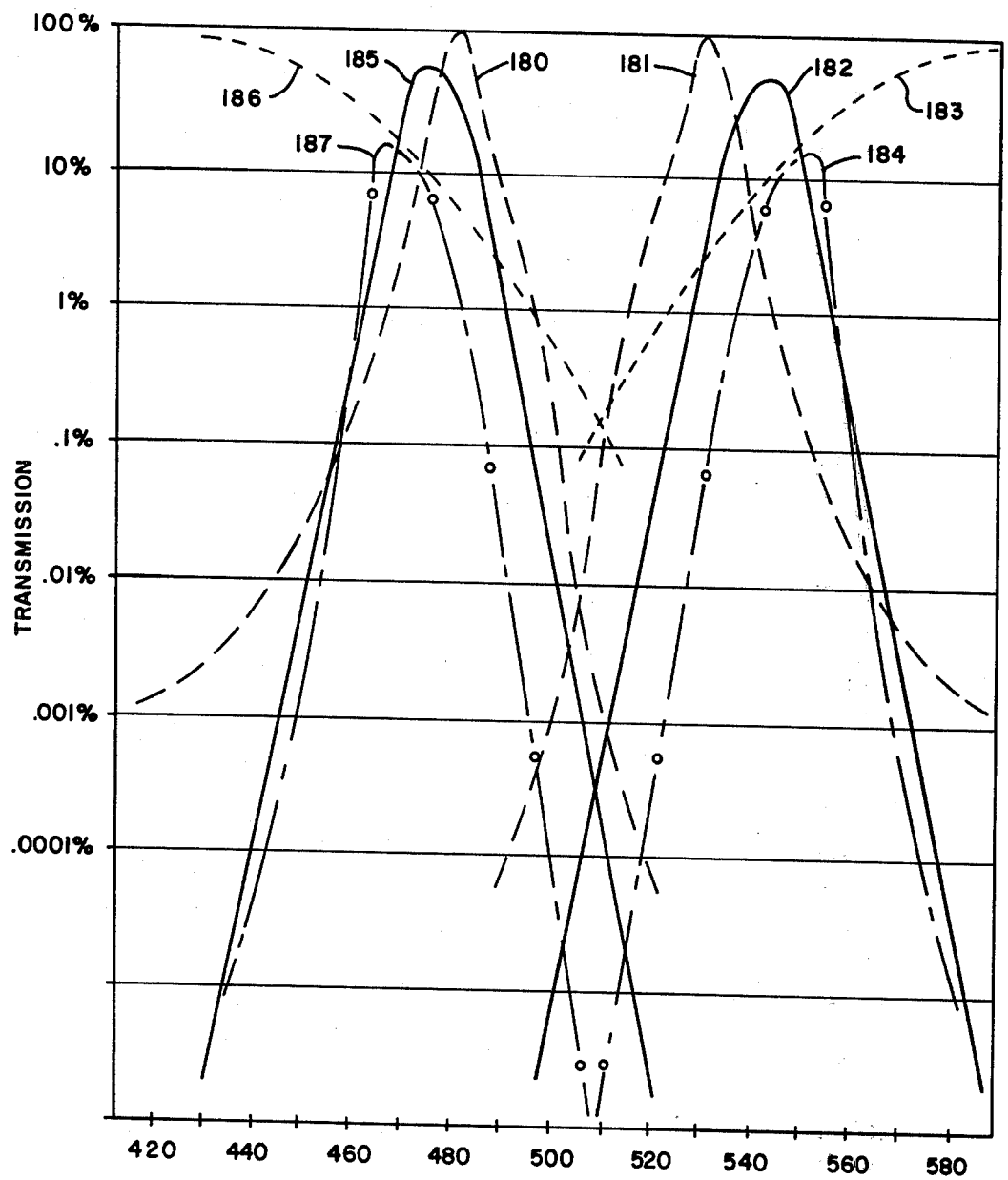
FIG.—14

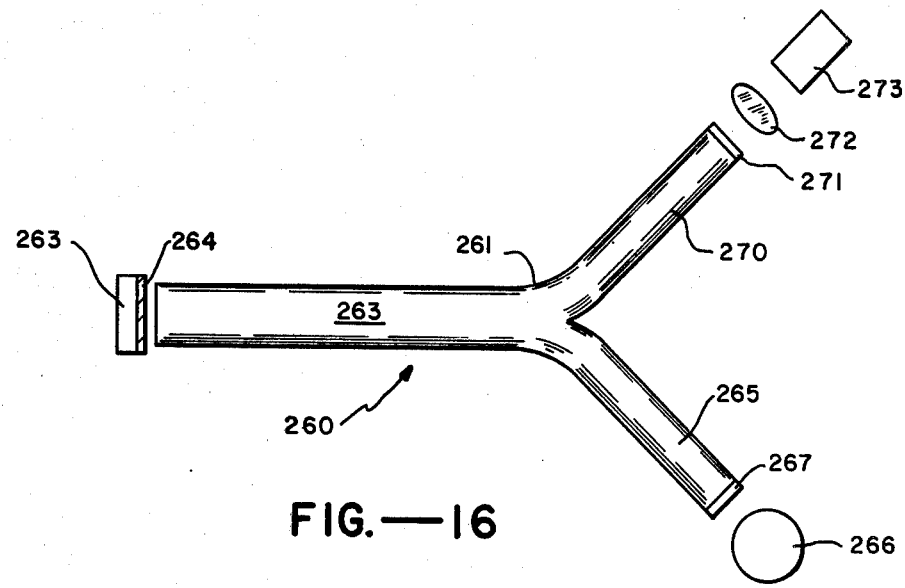
FIG.—16
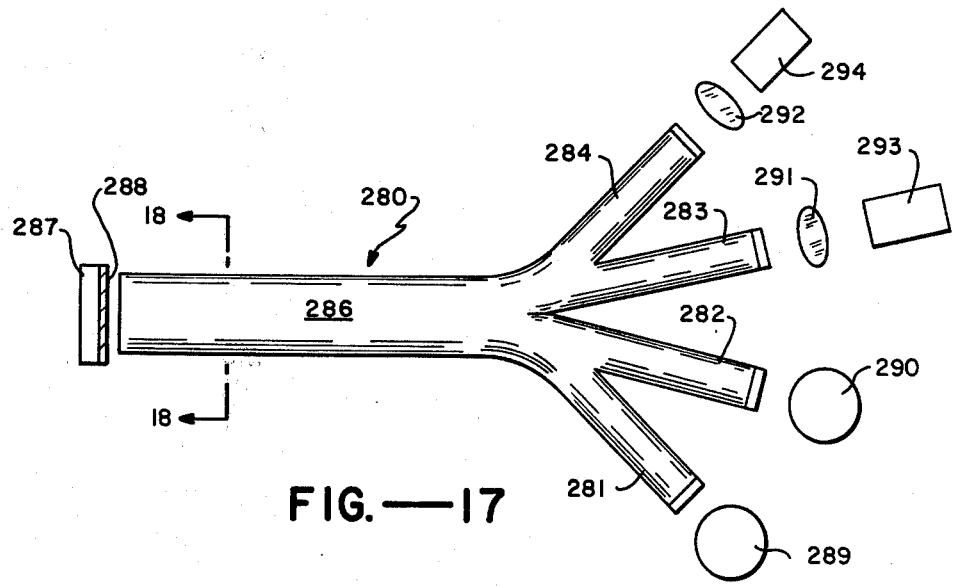
FIG.—17
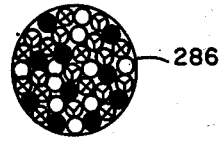
FIG.—18

FLUOROMETRIC SYSTEM, METHOD AND TEST ARTICLE

CROSS-REFERENCE TO RELATED APPLICATION

This application is a continuation of application Ser. No. 703,579 (filed 7/8/76 now U.S. Pat. No. 4,056,724) which was in turn a continuation-in-part of application Ser. No. 447,574 filed Mar. 4, 1974 now U.S. Pat. No. 3,913,687 and of Ser. No. 553,582 filed Feb. 27, 1975 now U.S. Pat. No. 3,992,631 issued Nov. 16, 1976.

BACKGROUND OF THE INVENTION

This invention relates to fluorometric systems for the detection of sample substances derived from biological fluid or tissue tagged with fluorochromes and to fluorometers adapted for more accurate measurements of surface mounted fluorescent samples. It is particularly useful in the detection of hormones, enzymes, drugs and other substances.

Most infectious diseases of bacterial or viral nature produce antibodies in the blood serum of the subject. This provides a degree of immunity against future assaults by the identical infectious agent or antigen. One method for detecting the presence of a particular antigen is to add to it a specific antibody which binds to the antigen. If the antibody has been previously tagged with a radioactive element (RIA technique) or a fluorescent dye, which does not interfere with its immunological properties, the coupled comples can be detected by an appropriate detector; and, in the case of the fluorescent additive, can be at best semiquantitatively measured, as is done in cases in the prior art on a microscope slide for visual inspection.

There are many reasons why RIA is not completely satisfactory. For example, in the presence of small quantities of antigen, only few counts per second can be detected. Since the "noise" of the system is proportional to the square root of the signal count, large errors in accuracy are made at low signal levels. Furthermore, radioisotopes have a limited shelf life due to half life decay, and require special licensing, handling and disposal.

Testing which relies on fluorescense tagging techniques, as heretofore known, has been qualitative, or at best, semiquantitative as an assay. In the area of the largest diagnostic use of fluorometry (i.e. immumofluorescense microscopy in which samples are typically mounted on a microscope stage and illuminated with an exciting wavelength) the fluorescence is observed through the stage with appropriate filters interposed to select the wavelength to be observed. Typically, the resultant observation is recorded by a laboratory technician as a comparative degree of fluorescence, for example, 0, +1, +2, +3, or +4 by comparison to known reference concentrations. In some instances, where blood titre or concentration of antibodies is the desired unknown, the technician prepares a number of slides; on each is a different concentration of the test material. Thus, the technician may estimate a +4 reaction in the microscope when the blood serum or the bacteria broth medium was diluted 1:4 in distilled water, or 1:16, or 1:128, etc. It would be of great advantage to medical and clinical authorities if a fluorometer could automatically and quantitatively read titre or concentration quickly and accurately, without the necessity of making serial dilutions.

To accomplish the foregoing known systems use a very powerful light source and cause a phenomenon known as photobleaching. Sometimes photobleaching is so rapid that the system has to be shut-off and allowed to return to chemical stability over a certain period of time before another attempt at a reading can be made. In addition, also, it is found that the light itself which is used is usually so powerful that it causes photochemical reactions and loss of signal. Attempts to mechanize and make systems of the foregoing type quantitative have primarily relied on the use of complicated electronic computing systems which observe the ratios of the variable being measured, compute the slope of fading or photobleaching effects that are observed and extrapolate these back to an assumed zero time.

Both liquid scanning and surface scanning fluorometers are known and will be discussed. Liquid scanning respect to fluorometers usually utilize a cuvette in which a liquid containing the substance is disposed, through which excitation light is passed and from which the emitted fluorescence is observed normally in a right angle configuration. It has been found that these systems are unsuitable for the present applications primarily because liquid systems and cuvettes themselves, apart from the sample being investigated all contribute very substantial background fluorescense, so that, unless a very high degree of careful chemical separation is utilized together with extremely well controlled materials selected to have low fluorescence in the wavelengths of interest, such systems are unsuitable. Attemps to adapt these instruments for surface measurements have not been particularily successful. Such systems are typically inefficient and have not provided for the descrete handling of individual samples. In general past fluorometers and RIA systems have been unduly sensitive to background and non-sample oriented signals. There is therefore, a need for a new and improved fluorometric system.

SUMMARY OF THE INVENTION AND OBJECTS

In general it is an object of the present invention to provide a fluorometric system and method which will overcome the above limitations and disadvantages. Another object of the invention is to provide a fluorometric system of the above character which is quantitative, which is easily calibrated and which is arranged to efficiently operate within acceptable limits relating to photobleaching and fading. Another object of the invention is to provide an improved optical fluorometer particularily adapted to read samples disposed on a carrier having and presenting a free sample surface thereon, and in which the optical system receives fluorometric data solely from the sample area of said carrier. Another object of the invention is to provide both fiberoptic and lens optical fluorometric systems for carrying out the invention.

The fluorometric system of the present invention measures a sample substance coated over a surface on a solid substrate. It includes a source of light filtered to selectively excite fluorescense in the sample and light-conducting means for conducting light from the source to the sample. Emitted lightdetector means captures and determines the intensity of fluorescence emitted from the sample substance by converting the flourescent light intensity to an electrical signal by a photodetector. Fluorescence is conveyed from the sample area to the photodetector by suitable light-collection optics terminating adjacent the sample. the optical parameters of the various elements interposed between the sample and photodetector define a light path which is constructed and arranged in accordance with this invention to prevent excessive loss of fluorescence (i.e., cumulative loss is held less than 95%). Thus, the disclosed light-collection optics (such as fiber optical cables or lenses) must be constructed with limited gap distances at each end and with a large collection aperture in order to enable efficiency of this level to be obtained over the emission band peak.

An additional and related criteria is that the foregoing must be achieved within the constraint that the input light intensity must be held to a value less than causes photo-bleaching or photo-disassociative effects greater than that which results in a fading rate of one (1%) percent per minute. By achieving specifications that meet the foregoing, a very useful and accurate instrument is disclosed.

The coated substrate to be viewed in the fluorometer may comprise a single sample coating on a body. Alternatively, a body adapted to enable detection and determination of more than one sample substance may include multiple spaced coating areas (e.g., bands) of different substances. A single coated area may include different substances in random dispersion tagged with different fluorochromes.

In one embodiment, the fluorometric system includes a branched fiber optical cable for conducting light from the source to the sample and for conducting emitted fluorescent light from the sample to the detector. One branch conducts light from the source to the sample and the other conducts the fluorescent light to the detector. These branches meet in a common fiber bundle terminating at the light input end. In this manner, the area of coincident excitation and emission is maximized at extremely close gap distances and optical efficiency is obtained.

Another advantageous fiber optical system includes at least two fiber optical cables for conducting the emitted light to the detector and means for alternating the input to the detector between the cables. This system can read at least two coated areas on a single substrate without movement of the substrate as in a comparision between a standard quantity of sample and one or more unknown samples. Similarly, both the light conducting means to excite fluorescence and to receive fluorescence comprise branched optical cables for transmitting multiple wavelengths of light to the sample and receiving different fluorescent signals.

A third preferred embodiment constructed in accordance with the present invention uses lenses systems intersecting a removable stage forming an analysis test station. The stage is adapted to receive a member having a surface forming a carrier to a fluorometrically active sample substance adhered thereto and presenting a free surface for examination. The member carrying the sample is constructed and arranged for insertion and removal from the stage independently thereof and is adapted to form a light-tight arrangement with the stage so as to exclude background light from the optical systems. In addition, the stage and carrier member together with the associated optical components and housings serve to also form an enclosure for the sample contained therein which enclosure avoids the circulation of ambient atmosphere (i.e., usually air). In this preferred embodiment the surface portion is arranged horizontally and includes a slight depression so that the sample may be disposed thereon in liquid form and so remain to present a free liquid surface for exposure and examination during the analysis. By means of the foregoing, the sample is maintained quiescent in movement and in a stable, low evaporative environment for analysis. As in the previous embodiment, the optical systems maintain the excitation light intensity and collection efficiencies within the limits defined by the present invention, as will be more clear from the detailed description herein.

In each of the foregoing embodiments filters are utilized for defining the input and excitation wavelength band and for establishing a band width of sensitivity in the detection system. For optimum performance, these filters have been found to be very critical and detailed specification for their selection will be given.

These and other objections and features of the present invention will become apparent from the following detailed description of the preferred embodiments when taken in conjunction with the accompanying drawings, of which:

BRIEF DESCRIPTION OF THE DRAWINGS

FIG. 7 is a graph relating concentration of fluorescent material in sample (C) and intensity of detected signal ($I_O$) as a function of efficiency of the optical collection system and as a function of input light intensity;

FIG. 8 is a schematic, isometric view of another preferred embodiment of fluorometer constructed in accordance with the present invention, shown with external portions in phantom lines;

FIG. 9 is a detailed optical diagram of the fluorometer of FIG. 8;

FIG. 10 is a perspective view of a test stage assembly including sample holder constructed in accordance with the present invention and particularly adapted for use in the fluorometer of FIG. 8;

FIG. 11 is a cross-sectional view, in elevation, of the test stage assembly of FIG. 10;

FIG. 12 is a cross-sectional view taken along the lines 12—12 of FIG. 11;

FIG. 13 is a top plan view of the sample holder of FIG. 10;

FIG. 14 is a graph depicting performance curves of filters constructed in accordance with the present invention for use in the embodiments of FIGS. 8–13;

FIG. 15 is a block diagram of an electronic circuit for use in the fluorometer of FIGS. 8–14;

FIGS. 16 and 17 are schematic views similar to that of FIG. 1 of modified forms of fiber-optic fluorometers constructed in accordance wth the present invention; and FIG. 18 is a cross-sectional view of a fiber-optic cable taken along the lines 17—17 of FIG. 16.

DESCRIPTION OF THE PREFERRED EMBODIMENTS

The present invention relates to a fluorometric system and method to quantitatively detect and measure a fluorescent sample substance coated as a layer on a substrate. As defined herein, the term "fluoresent sample substance" is one which includes a material derived from either a biological fluid or tissue and which, alone or in combination with other materials, emits fluorescence upon excitation with a selected wavelength of light in a solid layer form. Common fluorescent sample substances include autofluorogenic material derived from a biological fluid (e.g., tetracycline), materials derived from such fluids tagged with fluorochrome before or after isolation, materials derived from such fluids linked in the layer with homologous fluorochrome-tagged materials (e.g., antigen or antibody, one of which has been tagged with a fluorochrome). The present description will make particular reference to the last named substance.

Figure 1:
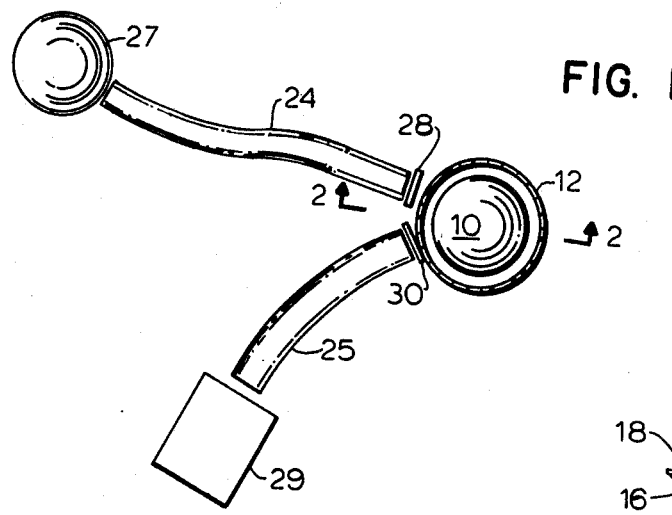
FIG. 1 is a top, schematic view of one embodiment of a fluorometric system constructed in accordance with the present invention using fiber bundle optical systems.
Figure 2:
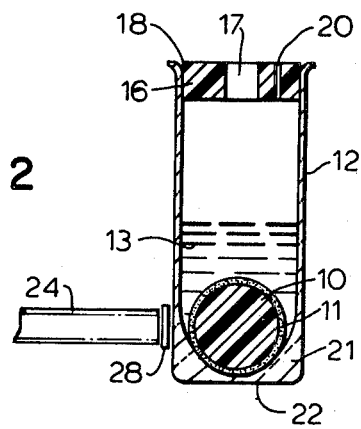
FIG. 2 is a cross-sectional view, in elevation, taken along the lines 2—2 of FIG. 1.

Referring now to the embodiment of the invention as shown in FIGS. 1 and 2, there is provided a member 10 having a surface portion adapted for forming a carrier for a fluorometric substance which is adhered thereto as a surface coating. In the embodiment shown, this member is in the form of a ball which is prepared, by way of example, in the following manner.

The ball may be about 10 mm in diameter and made of plastic, e.g., nylon, and bears a dried film or coating 11 of an antibody related to the antigen to be determined, e.g. to Australian antigen. Since coatng of all balls will be done at substantially the same temperature (37° C.), and for substantially the same incubation period (30 minutes), each ball will have substantially the same amount of antibody on it, which is important for quantitative results. The ball is typically on the order of 5–20 mm in diameter so that an area at least one square mm is viewed by the fluorometer. The ball is placed into a cuvette 12, in this instance of 12 mm inner diameter. It is preferred that fluorescence measurements are made in accordance with the present invention by viewing the surface to which the fluorometrically active substance is adhered by optical systems which are very closely positioned with respect to that surface so as to maintain a predetermined level of optical efficiency. However, if fluorescence is to be detected and measured with the ball in a cuvette, as shown in FIG. 1, the cuvette must be formed by a material, e.g. glass, which is non-fluorescing at the wavelength to be measured.

Referring now particularly to FIG. 2, an example is now given of the preparation of the ball, it being understood that this description is specific for the sake of giving a detailed background on one procedure for such preparation. However, it is to be understood that it is given soley by way of example and that many other procedures will be found useful and in accordance with the present invention. Examples of such procedures are given in co-referenced application Ser. No. 553,582 in greater detail in conjunction with many other illustrations and examples of the use of the fluorometric system set forth herein, the content of which application is not deemed necessary for understanding the invention as presented and claimed herein, and, accordingly, will not be repeated but is incorporated herein by reference.

The ball is placed in a cuvette 12. One ml. of serum 13 from a patient or subject is added to cover the ball and the cuvette is gently rocked for 5 minutes to obtain room temperature incubation. Australian antigen 14, if present, binds to the coating 11 of antibody on the ball. A cap 16 having a hole 17 is placed on the open end 18 of the cuvette 12 and the cuvette 12 is inverted, permitting the serum to run out. A small second hole 20 to permit passage of air is also provided in the cap 16. Suitably, the cuvette 12 has a rounded or generally hemispherical inner surface 21 at its base 22, whereby the ball 10 is held in position and does not move or roll around during the fluorescence test.

After incubation with the subject serum, the cuvette is rinsed out, e.g. with aqueous phosphate buffer or distilled water, which is then also allowed to pour out of hole 17, the ball 10 remaining in the cuvette and antibody solution tagged with a substance which fluoresces under ultraviolet light. Such a fluorescent tag or label substance can be, e.g. sodium fluorescein isothiocyanate or other suitable substance. However, sodium fluorescein isothiocyanate, with excitation at 460 nanometers and emission at 520 nanometers, is advantageous. The material in the cuvette 12 is again incubated as described above, the liquid poured off and the cuvette and ball rinsed as before. The ball now bears the antigen and attached fluorescent substance 23 where Australian antigen is present. The cuvette 12 and/or member 10 are now ready for insertion into the fluorometer system.

Figure 3:
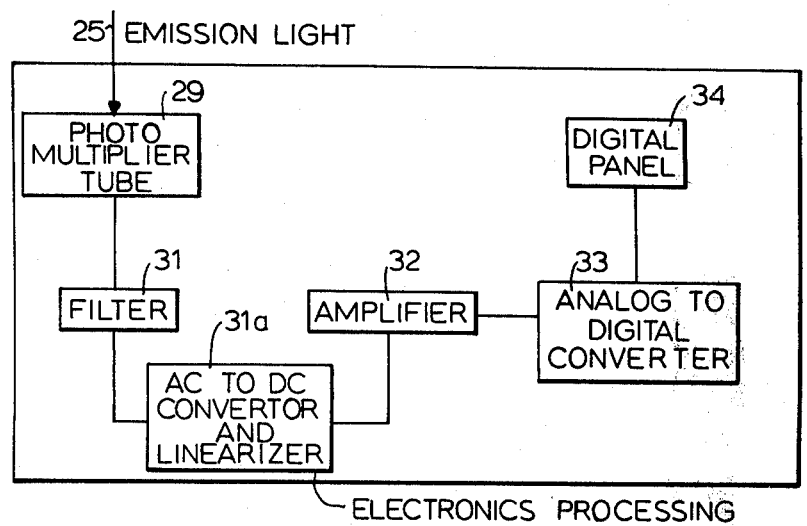
FIG. 3 is a schematic diagram of the photodetector and associated circuitry for use in the embodiment of FIG. 1.

Referring now to FIGS. 1 and 3 in the fluorometer system, the member 10 and/or cuvette 12 is so placed that a fiber optical cable 24 conducts ultraviolet light from a light source 27, which can be any desired source which includes the excitation wavelength. The light then passes through a gelatin filter 28, which ensures that only light of the exciting wavelength and excluding the emission wavelength reaches the carrier surface on member 10 to excite fluorescence of the coupled substance 23. A second fiber optic cable 25 is disposed preferably at a small angle, less than 30°, from the cable 24; and the emitted fluorescence passes through a gelatin filter 30, which ensures that only emitted fluorescence reaches photodetector (e.g. a photomultiplier) and associated circuitry 29 via the fiber optic cable 25. The photodetector 29 converts the intensity of the emitted fluorescent light into an electronic signal. This signal is passed through a filter 31 to a processor 31a (which converts the AC signal to a DC signal, e.g. through a peak-to-peak detector and linearizes the relationship between fluorescent light intensity and DC voltage, as by a four-step diode linearizer), an amplifier 32, and an analog-to-digital converter 33 and then is displayed on a digital panel meter 34 calibrated directly in titre.

Figure 4:
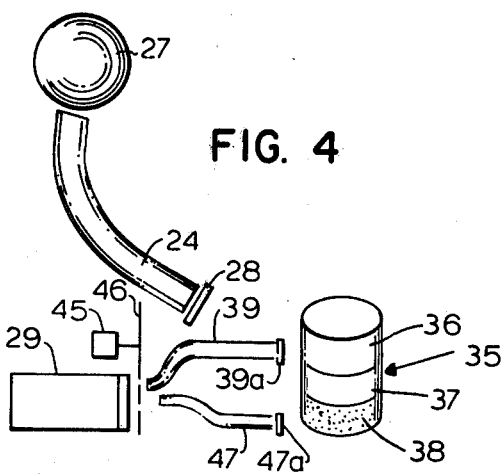
FIG. 4 is a schematic view of another embodiment of the fluorometric system constructed in accordance with the present invention utilizing a sample carrier in the form of a cylinder.

In the embodiment shown in FIG. 4, a nylon cylinder 35 is employed as a carrier member 10 instead of the ball shape. The upper portion of the cylinder 35 is coated with a standard fluorescent coating 36, i.e. of the same fluorescent substance as is used to tag the antibody coating 38 of the lower portion of the cylinder 35 and has a known titre as measured on the detector device which is employed in the test or assay; in this instance, the fluorometer described herein. A blank space 37 is left around the surface of cylinder 35, separating the upper and lower coating, 36 and 38, respectively. The lower coating 38 contains, for example, streptococcal fluoroescent-tagged antibody, being prepared in the same manner as described above with respect to the member 10, except that only the lower portion is immersed in the body of liquid serum to determine if any of the suspected antigen or antibody is present in the serum being tested. In this embodiment, the ultraviolet light source 27, the fiber optical cable 24, and the filter 28 are again provided. Two fiber optic cables 39 and 47 are provided with respective filters 39a and 47a. One such cable 39 conducts fluorescent light from the standard fluorescent coating to the photomultiplier tube 29, and the other such cable 47 conducts emitted fluorescence from the lower coating 38 to the photomultiplier tube 29. A chopper wheel 46 operated by a motor 45 revolves and alternates the flow of light from each coating 36 and 38 to the tube 29. In this manner, a direct comparison is obtained between the standard reference and the test portions.

Figure 5:
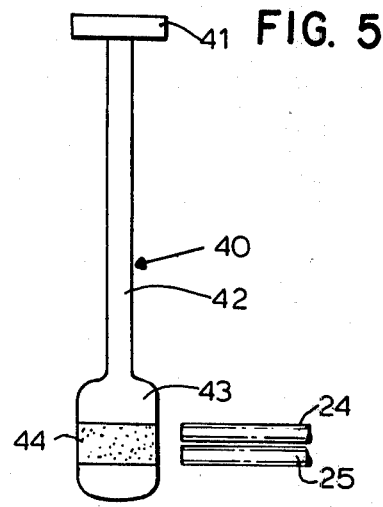
FIG. 5 is a schematic view of an alternate sample member configuration constructed in accordance with the present invention.

In the embodiment of FIG. 5, the carrier member 10 comprises a paddle-shaped body 40 having a handle 41 at one end extending out of the cuvette 12, a stem 42, and a wide, flat head 43 at the other end, the head 43 bearing a coating 44 of sample. In this embodiment, the two fiber optic cables 24 (for excitation light) and 25 (for emitted fluorescent light) are parallel to each other, or at an angle of 0° with respect to each other. Conveniently, the two cables 24 and 25 can also be arranged as a coaxial cable. The other elements of the device and system are as previously described and shown.

Figure 6:
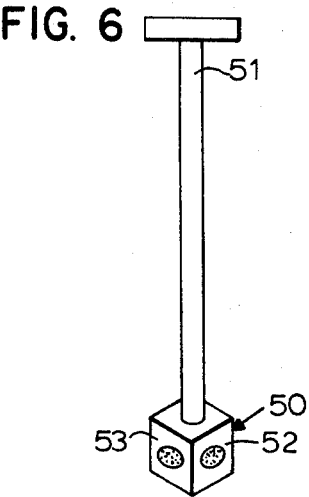
FIG. 6 is a schematic view of another alternate sample member configuration constructed in accordance with the present invention.

Another embodiment of multiple test sample carrier body is shown in FIG. 6. Here, the body is a cube 50 at the end of a handle 51. The cube 50 can present four faces, two faces 52 and 53 being visible. Each face has a different sample. Four different fluorescent tags can be provided, and the fluorometer may have a filter wheel with four selected wavelength regions to isolate energy going to the photodetector 29.

The following description of FIGS. 7–14 relates to a commercially developed fluorometer developed in accordance with the present invention. Before proceeding further, it will be helpful to consider certain limitations and restraints which are placed upon the fluorometer of the present invention in order to achieve the required performance levels.

In general, fluorescence from a sample may be expressed as follows:

Where $I_F$ is fluorescent intensity; $I_X$ is excitation intensity; $\phi$ is quantum efficiency; and E, B are geometric factors $$I_F = I_X \phi (1 - e^{-EBC})$$

For small concentration of C on a surface $$e^{-EBC} = 1 - EBC$$

then $$I_F = I_X \phi EBC$$

Let $K = \phi EB$, a physical and geometrical constant for the substance and system, then $$I_F = I_X K C \qquad (1)$$

Define $I_X = E_i I_s$ and $I_o = E_o I_F$ where $I_S$ is source intensity; $I_D$ is intensity at detector; $E_i$ is light transmissive efficiency from source to sample; and $E_O$ is light transmissive efficiency from sample to detector, then $$I_D = K E_i E_O I_s C \qquad (2)$$

Fluorescence fading occurs at high intensities $$I_{F(t)} = K I_X C e^{-kt}$$

where $k = k_o I_X$ and $k_o$ is a rate constant for decomposition then $$I_{D(t)} = K E_i E_O I_s C e^{-k_o E_i I_s t}$$

For small values of t (short times)

$$e^{-k_o E_i I_s t} = 1 - k_o E_i I_s t$$

then $$I_{D(t)} = K E_i E_O I_s C (1 - k_o E_i I_s t) \qquad (3)$$

For a practical limit, fading should be less than 1% per minute and this value is given predominantly in that desirable laboratory procedure accomplishment time is one minute and that the largest amount of fading that is acceptable is of the order of 1% per minute. Given these constraints, the following equations hold:

$$0.99 K E_i E_O I_s C = K E_i E_O I_s C - \frac{K k_o}{E_O}(E_i E_O I_s)^2 C$$

and $$0.01 E_i E_O I_s = \frac{k_o}{E_O}(E_i E_O I_s)^2$$

$$0.01 = k_o E_i I_s$$

$$\therefore I_s \leq \frac{0.01}{k_o E_i} \qquad (4)$$

Substituting (4) into (2)

$$I_D = \frac{0.01 E_O}{k_o} C \qquad (5)$$

The variables of Equation 5 are illustrated in the graph of FIG. 7 wherein the line 100 represents the one (1%) percent fading rate at 100% efficiency ($E_o = 1.0$). Above and to the left of this line, high powers of input light intensity are required and are found to cause photobleaching and fading at an unacceptable level and, therefore, cannot be used in this invention.

With the optical systems disclosed herein, it is possible to achieve efficiencies of the order of 5%, the 5% line being indicated at 101 for illustration. The claimed operating domain 103 of the present invention lies between lines 100 and 101. As shown, this domain extends down to the limit where the signal and background become comparable in strength (S/N = 2.0 being indicated at 102) at least to which satisfactory performance is provided by the present invention. Below about 5% efficiency, it becomes impossible to detect low concentrations of sample. It is also seen that the fading rate limit and efficiency requirement are mutually interdependent and must both be satisfied. Accordingly, the use of the optical systems disclosed herein achieves an efficiency of greater than 5% in the collection and detection systems and the input light intensities are held to values such that the fading rate is less than one (1% percent per minute.

Referring now more particularly to FIG. 8, there is shown such a lens type fluorometer, the overall outward appearance of which is shown in the phantom lines. The optical system of the fluorometer is developed within an opaque block 104 of plastic, as for example Delrin, selected because of its dimensional and thermal stability. The block is machined to accept the various components as shown in the drawings. The details of the machining are not believed esssential to understanding the invention and, accordingly, they have been omitted for the sake of clarity.

Referring simultaneously to FIGS. 8 and 9, the system generally consists of three major optical systems: An illumination optical system 105 for supplying excitation light to the sample; a collection optical system 106 for receiving fluorescent output from the sample; and a reference level optical system 107 for periodically establishing and checking zero and preset intensity levels.

The illumination optical system 105 consists of lamp 110, condensing lens 111, excitation filter 112, chopper 113 and its lens system 114a and 114b, as driven by an electric synchronous motor 115 and focusing lens 116 for imaging excitation light onto a test stage 150 including sample 118.

The collection optical system 106 consists of a collecting lens 120, emission filter 121, and photodetector lens 123 which images the sample member surface onto a photodetector 124.

The reference level optical system 107 consists of a beam-splitter 130, a turning mirror 131, chopper 113 and associated reference lens system 133, a diffusing screen 134, a portion of which is developed by lens 135 and re-inserted at beam splitter 136 into the collection optical system 106. Rotation of the chopper 113 causes light to pass alternately through the illumination optical system 105 or through the reference optical system 107. Thus the output at the detector is an alternating signal during one period of which the intensity of the excitation source is measured while the other period measures the fluroescent output.

Many of the optical components shown and described heein could be selected from a wide variety of available more complex designs, but the following have been found to be particularly satisfactory for use in the present invention. All of the lenses are of aspheric type and are standard products of Mells Griot, product 01 LAG 005. These lenses have f/0.75 and are planar on the non-aspheric side. Lens 120 which collects the light from the sample station is the only lens for which a substitution is not readily available in view of the large aperture and solid angle of collection required of that lens (f/0.75 planar side focal length).

FIG. 9 contains ray tracing lines thereon which serve to illustrate the functions of the lenses and optical components. Thus, lens 111 collimates the light from the light source and passes it in parallel rays through the first filter at 112 after which the beam-splitter 130 divides off a certain portion of the light to be delivered to the reference optical system 107. The remainder passes to the chopper lens pair 114 in the excitation optical system 105. The first lens of this pair 114a focuses the light down to a small spot so that the cut-off and cut-on times and general level of intensity of light exiting from the chopper is well-defined in value over an appropriate period of time. The second lens 114b of that pair collimates the light for delivery to a focusing lens 116 which brings an image of the filament down into a small focused spot on a central area of the sample carrier at 118.

The output from the sample is collected by planoapheric lens 120 over a wide solid angle and delivered in parallel rays through the emission filter 121, through a beam insertion device 136, and thence focused by detector lens 123 onto the active element of the photodetector 124.

The portion of the beam which is removed for reference purposes is turned by turning mirror 131 to follow a path parallel to and alongside the excitation path. This light is passed through lens pair 133 which also brings the light source to a focus in the plane of the chopper so as to also provide for rapid turn-on, turn-off, and well-defined value of intensity when the reference beam is on. The reference beam is then passed in parallel rays to a diffusing screen which can consist of a film of polyester, such as that made by DuPont (Type A), having a dull matte finish on the side facing the detection system 106. The matte finish serves as a light scattering function and thus converts the film into a secondary or reference source of high uniformity. A portion of the central area of the film is taken by lens 135 and the rays made parallel for being passed to insertion mirror (partial) 136 lying in the collection stream path between the emission filter 121 and the photodetector focusing lens 123.

Referring now more particularly to FIGS. 10-13, the sample carrier stage 150 is shown in detail. This stage is removable in its entirety to facilitate cleaning. As will be noted from FIGS. 10-12, the stage is inserted into a cylindrical passageway in block 104 at a lowermost position such that the carrier 118 containing the sample thereon faces upwardly and in a substantially horizontal plane within the assembly as a whole. By making this provision, together with certain structural features of the sample carrier, it is possible to insert and measure a sample having a substantially free liquid surface while simultaneously maintaining that surface free of changes during analysis (such as by evaporation). The stage is rotationally oriented for insertion into the optical block 104 by virtue of an elongate axial slot 151 formed along one side of the stage and adapted to accommodate a locating pin 152 mounted in the optical block. A similar locating pin 152 projecting in the elongate slot 151 indicates when the stage has been brought to a fully inserted position within the block.

The sample carrier 118 is mounted on a removable sample carrier member in the form of a spatula 154 (shown inserted in FIGS. 10 and 11 and separately in FIG. 13) consisting of an end portion 155 having a substantially planar surface 156 and an area of slight depression 157 formed at that end of the member on which carrier 118 is disposed to form a support for a liquid film or droplet of sample. The spatula 154 further consists of an elongate blade 158 having a registry projection 159 thereon and terminates at its other end in a paddle 160 suitable for being easily gripped by the operator. The spatula is easily removed and inserted into the stage, the latter normally remaining in place within the instrument. Thus, an elongate slot 162 is provided within the stage for receiving the member, together with an upwardly extending groove 163 which accommodates projection 159. When fully home, the parts appear as shown in FIG. 11. It will be further noted that the outward extremity of the mounting recess 162 (at 164) is provided with a converging wedge-shaped configuration so that when the spatula is fully seated, the end 166 thereof is urged downwardly against the floor of slot 162 into precisely positioned contact within the stage. With the utilization of plastic parts for many of the components, it is found preferably that these components be restrained laterally and in every other dimensions so that any slight warpage of the plastic parts of which the carrier member is made is compensated for, the member being urged into exact position against the bottom of slot 162 within the analysis stage. Consideration of the optical diagram with respect to the focusing of light onto the stage and to the carrier spatula and the collection of light therefrom as shown in FIG. 9 will explain the need for the relieved portions 168, 169 provided by the removed portions of the end of stage 150 and laterally located adjacent the sample 118. Once positioned, member 154 is maintained in position by virtue of urging contact made by spring-loaded ball 170 carried in the body 104 of the optical system and adapted to engage and urge the back surface of projection 159. In addition, ball 170 falls behind that back surface and assumes a position serving together with the projection itselt to block light from passing through the channel 162 and capable, it not blocked, of causing non-dark background readings. An aperture 172 is provided through the stage and passes light from a small light-emitting diode 173 to a small light detector 174. This aperture is closed by the passing of the member 154 as the same is pushed into the unit and when closed provides a "ready" signal for the associated electronics. An additional aperture 176 extends from the region immediately below the sample carrying end of member 154 and in general alignment with the excitation light beam so that a photodetector 178 positioned immediately behind this second aperture indicates when the sample is actually in position and blocking light from the beam.

It is a particular feature of the present invention that the carrier stage 150, even though removable together with its independently removable sample carrier member 154, nevertheless when assembled forms both a light-tight and air-tight enclosure within the optical assembly. The former eliminates background light; the latter stabilizes the sample volumn so that a liquid sample having a free surface at 118 does not change configuration or character from evaporation during the measurement period. The latter generally quiescent enclosure is defined and formed by the carrier member 154 itself which closes aperture 176, by the stage and its close fitting relationship with the adjacent block, and by lenses 116 and 128, both of which are sealed into contact within bores supporting the respective excitation and collection optical systems.

In constructing the fluorometer in accordance with the present invention, it is important that the emission filter design be carefully selected, and that the excitation filter design compliment that of the emission filter design. In the following discussion, excitation and emission filter will be disclosed which are of substantially identical (although complimentary) structure and which are produced by inteference layering techniques in accordance with applicant's specifications and with particular reference to application in the present invention. The examples will be given in connection with filters designed for use with fluoroscene dye which has an absorption frequency band at approximately 480nm (blue) and an emission frequency band at approximately 530nm (green). This dye is widely used because of its high quantum efficiency, i.e. about 80–90% of the input radiation that is absorbed is re-emitted.

Referring now to FIG. 14 there is shown a series of curves which illustrate the absorption and emission bands 140, 142 as well as the contours of the characteristics of the filters which are constructed in accordance with the present invention. In general, it is desired to obtain a compromise wherein the maximum available input radiation is applied to the sample while obtaining the maximum output fluorescence emission without overlap or cross-talk betwen the illumination and collection channels. Since the absorption band 180 of fluorescence and the emission band 181 overlap each other, there are certain techniques which must be used to obtain optimum performance. In general, the present filters are characterized as follows: a combination pass band, plus cut-on (or cut-off), filters developed by interference coatings laid upon a single substrate. By doing so, it is possible to obtain a high transmission filter having very high rejection of the adjacent channel.

Thus, the emission collection filter 121 includes a three-cavity pass band type having a wavelength of highest transmission at 540nm and half-width of 16 nm for 50% transmission. This is combined with a cut-on filter having a through transmission frequency at 550nm of 80%. The pass band curve is shown at 182 while the cut-on curve of this filter is shown at 183 in FIG. 14 while the combination filter taken together is shown as curve 184. The illumination filter 112 is similarly constructed with a pass band curve having a center wavelength of 475nm with half-band width of 16nm, combined with a cut-off filter having its 80% transmission at 465nm and incorporated with the pass band filter on a single substrate to form a combination filter of very satisfactory performance. The excitation pass band curve is shown at 185, the cut-off curve is shown at 146 and the combination illumination filter at curve 187. The following are the specific specifications of interference filters which were made to applicant's specifications and which are available from Ditric Optics, Inc. of Marlboro, Massachusetts.

| Illumination Interference Filter | |
| --- | --- |
| CWL: | 475nm ± 3nm |
| HBW: | 12 to 17nm |
| %T: | ≧ 50% |
| BLOCKING: | ≧ 4 O.D. outside of passband to 1200nm ≧ 6 O.D. from 520nm to 540nm |
| Collection (Emission) Interference Filter | |
| CWL: | 540nm ± 3nm |
| HBW: | 12 to 17nm |
| %T: | ≧ 50% |
| BLOCKING: | ≧ 4 O.D. outside of passband to 1200nm ≧ 6 O.D. from 460nm to 490nm |

It will be noted that the crossband rejection is 6 O.D. or 0.0001% crosstalk between the channels.

The foregoing filters are generally manufactured by a technique known in interference filter manufacture as a three-cavity technique and may, of course, employ more cavities as the need may require. In general, it is found that the foregoing design in displacing the spectra maxima of the filters slightly away from each other and slightly off of the response characteristics of the dye, nevertheless provides very satisfactory performance. In addition, the use of cut-on and cut-off filters on the substrate with maximum transmissions of about 80% yields overall transmission of the desired band of the order of 40–50%.

Referring now to FIG. 15 there is shown electronic control circuitry which processes the output fluorometer of FIG. 8 for providing an output reading therefrom.

In general, the control circuitry serves to time demultiplex the output of the photomultiplier tube by suitable circuitry in demultiplexer 190 driven by a synchronizing pulse from a light emitting diode/detector pair 192 positioned across the path of the chopper 113 to derive a sample channel signal and a reference channel signal, the respective ones of which are processed in a sample channel and reference channel respectively. The channels include AC amplifiers 193a193b, demodulators 194a, 194b, and integrators 195a, 195b for developing DC signals S and R, the magnitude of which is proportional to the magnitude of signal strength as seen by the photodetector 124 when viewing the respective sample or reference channel. The DC signal outputs are passed through respective DC amplifiers 195a, 195b for isolation and applied to a ratio circuit, the output S/R of which is displayed on a digital display unit 198, and also is displayed digitally on the instrument's front panel at 198 shown in FIG. 8. By using this ratio technique, the stability of the unit is increased and electronic, photomultiplier and illumination lamp output drift is minimized.

FIG. 16 shows a modified form of fluorometer 260 of the fiber optic type in which a single branched fiber optic cable 261 replaces the two separate cables 224 and 225. A single-bundle portion 262 of the cable 261 leads to and away from a solid base 263 having a fluorescent surface 264. One branch 265 of the cable 261 transmits light from a lamp 266 or other light source and a suitable ("blue") filter 267 to the fluorescent surface 264. A second branch 270 of the same cable 261 conducts the emitted fluorescence from the surface 264 to a suitable ("green") filter 271 and thence through a lens 272 to a solid state or photomultiplier type of detector 273. Operation is basically the same as in FIG. 1 with readily apparent differences.

FIG. 17 shows another modified form of fluorometer of the fiber optic type 280 in which branches 265 and 270 of fiber optic cable 261 replaced with branch fiber optic cables 281, 282, 283, and 284, respectively. A single-bundled portion 286 of the cable leads to and away from a single base 287 having a fluorescent surface 288. Branches 281 and 282 transmit light from lamps 289 and 290, respectively, or other light sources, to fluorescent surfaces 288. Branches 283 and 284 of the same cable 286 conduct the emitted fluorescent from the surface 288 through suitable lenses 291, 292, respectively, to solid state or photomultiplier type of detector 293 and 294, respectively.

One method for employing the device of FIG. 17 which is highly advantageous is to view surface 288 which includes a plurality of biologically derived substances in random dispersion. Each of the substances is tagged with a fluorochrome which emits fluorescence responsive to a different wavelength of light. Thus, lamps 289 and 290 emit the different fluorescence exciting wavelengths while the multiple fluorescence is received simultaneously by detectors 293 and 294 through light conducting branches 283 and 284, respectively. The multiple fluorochrome tagged substances in random dispersion may also be read using the single branched fiber optical cable of FIG. 16. In this instance, a single lamp or other lamp source replaces lamps 289 and 290 and a plurality of filters are employed to provide the proper wavelengths to excite the respective fluorochromes in the sample. Similarly, the light-conducting cables 283 and 284 may be replaced with a single cable and detectors 293 and 294 may be replaced with a single detector so long as the wavelengths to which the detector is responsive is synchronized to the selected fluorochrome to be excited.

Referring to FIG. 18, a cross-sectional view of the common fiber bundle 286 of the branched cable 280 is illustrated schematically in which the fibers of the various branches are enlarged for viewing clarity. Such fibers are schematically represented by a solid circle, an open circle, a circle containing "x" and a circle containing "y". It is apparent that the four different types of fibers in this particular arrangement are randomly dispersed. It may be desirable to accomplish a specific optical effect to arrange them schematically as in concentric circles, not shown, or to use fibers of different diameters. An important feature of the present fluorometric system is the maximization of fluorescent light which is received from the sample in accordance with the general criteria discussed in connection with FIG. 7. This is particularly important when the fluorescent substance is present at very low concentrations and illumination is held to low values in order to limit fading. In the fiber optic systems of FIGS. 16 and 17 this objective is accomplished by avoiding gap distances in the light path between the fluorescent substance and the means for converting the light intensity into an electrical signal for quantitative measurement. With a fiber optic cable conducting light from the light input and adjacent the sample to the conversion means, such gaps include the distance between the light input end and the sample substance and any distance between the optical cable and conversion means.

It has been set forth for average fluorescence intensity, at a minimum, the cumulative fluorescence loss across the above light path from sample to detector should not be greater than 95% of the fluorescence available for transmission along that path. Such losses do not include losses due to viewing only a portion of a fluorescent sample surface. To take this into account, such loss is related only to the fluorescent light emitted from the sample within an area defined by the light input end perimeter projected onto the sample surface. Although limiting the loss is fluorescence to 95% across the total light path is a significant improvement over conventional fluorometers, it is preferred to limit such loss to below 50 to 90%. At such loss levels, even minute quantities of sample may be detected and determined quantitatively.

The above considerations deal primarily with fiber optic cables and light pipes and the importance of their close proximity, as expressed by gap distance, to surfaces from which they receive and to which they deliver light. Light conducting systems may also contain such components as lenses to collect and focus light, mirrors to reflect and redirect it, and apertures through which light passes after dispersion. When components such as these receive light from a surface that is radiating it into a hemisphere, the amount of such light they capture is approximately proportional to that portion of pi steradians defined by the circumference of the area they project on the hemispherical surface generated by a radius equal to the gap distance between the light emitting surface and the component receiving it.

Based upon the above relationship, the circumference which permits loss of no greater than 95% of emitted fluorescence corresponds to one that will generate a solid angle no less than approximately 0.3 steradian. The solid angle of non-circular cross-section is defined as one generated by an equivalent circular area.

A study of the fluorometric systems of the present invention illustrate the percentage loss can be directly related to the ratio of the gap distance between the sample and the effective diameter of the light input end of the emitted light collection optical system. The term "effective diameter" means either the diameter of a light input end of circular cross-section or the equivalent diameter of a noncircular cross-section. This latter term may be approximated by reference to the formula:

area: $\pi d^2/4$

The effective diameter, $d'$, of non-circular cross-section is defined as $$\sqrt{\frac{4 \times \text{area}}{\pi}}.$$

Reference to the relationship of gap distance to effective diameter is based upon the approximate relationship that intensity of fluorescence is inversely proportional to the square of the distance from the fluorescent substance. This approximation does not take into account an increase in capture accomplished by minimizing the angle of reflectance, i.e., the angle between the light conducted to the fluorescent substance to excite fluorescence and that received by the light input end of the detector means. It has been found that this value is not as significant as the gap distance. It is apparent that the effective diameter of the light input end is significant since an increase in the area of that surface causes a corresponding increase in light captured.

Using the above calculations, a gap distance adjacent the sample which permits loss of no greater than approximately 95% of emitted fluorescence corresponds to a ratio of gap distance to effective diameter of the light input end of no greater than about 5:1. Similar calculations may be made to determine the theoretical ratio of other fluorescent loss percentages. It should be understood that this ratio is only an approximation. The same formula applies to other gap distances in the light path such as between the fiber optical cable and the portion of the detector which converts the light to an electrical signal and between any lenses and mirrors which may be employed in the light path.

The branched fiber optical system of FIGS. 10-17 is particularly effective in reducing to a minimum the gap distance which can be obtained to minimize loss of emitted fluorescence. This is based upon the principle that the only area of the fluorescent substance which can be received by the detector is where the light transmitted to the substance for exciting flurorescence coincides with the viewing area of the light input end of the detector. This can be accomplished with separate fiber optical cables as in FIG. 1 until a gap distance is reduced to relatively small values. As this reduction occurs, the area of coincidence of totally separate light exciting and light emitting cables continuously reduces. It is apparent that this may be a limiting factor on the gap distance and consequently may cause excessive fluorescence loss for a sample substance in extremely small quantities. On the other hand, the use of branched cables each including a plurality of light transmitting fibers which terminate in a common fiber bundle at the light input end enable the fluorometer to be disposed extremely close to the fluorescent sample without lack of coincidence. The only limit on this is when the gap distance approaches zero at which point the fine fibers of the fiber bundle act like independent cables.

The common fiber bundle is particularly effective in embodiments such as multiple branching of FIG. 17. Cables with separate light input and output ends for each of the branches of cable 280 would require a fairly substantial gap distance to assure a sufficient area of coincidence.

Another technique to avoid loss of fluorescence is to maintain the gap between the sample coating and light input end of the detector free of solid medium which prevents transmission of excessive quantities of fluorescent light. It has been found that glass or certain plastics (e.g., polystyrene) at moderate thicknesses of less than 0.05 inch causes a loss of fluorescence less than 30%. Although it is preferable to avoid the interposition of such a solid medium, such losses are acceptable if necessary or convenient to the system. For example, in the embodiment schematically illustrated in FIG. 1, it may be convenient to employ a thinwalled cuvette to retain a coated substrate of a spherical shape. If so, the cuvette should be formed of a material which does not cause the loss of the fluorescence in excess of 30%.

The above description makes reference to fiber optical cables as one preferred light conducting means. It should be understood that other optical conduits such as light pipes may also be employed in those instances where the distance does not require the use of common fiber optical bundles.

I claim:

1. In a method for analyzing a sample by fluorometric techniques, the steps of disposing said sample on a carrier member having a surface portion adapted for receiving and supporting said sample thereon as an exposed layer presenting a surface for analysis at an analysis location, illuminating said sample with excitation radiation from a first optical system intersecting said analysis location for delivering said radiation to the surface thereat, controlling the frequency of said illumination to limit the excitation radiation to a predetermined frequency band overlapping the absorption band of said fluorometrically active substance and being substantially non-emissive in the band of fluorometric re-emission of said substance, restricting the total intensity of radiation impinging at said analysis location to a value less than that which causes photo-bleaching and fading of the sample in excess of a value of one percent (1%) per minute, collecting fluorescence emitted from the exposed surface of said sample, using a second optical system intersecting said analysis location for receiving said fluorescence, filtering the collective fluorescence to restrict the sensitivity thereof to a frequency band overlapping the emission spectra of said fluorometrically active substance and to be substantially non-responsive in the band of excitation radiation, detecting and countering said collective fluorescence, said collecting, filtering and detecting steps having a combined efficiency of at least five percent (5%) over the emission band peak.

* * * * *